United States Patent [19]

Grange et al.

[11] 4,218,465

[45] Aug. 19, 1980

[54] GLYOXYLIC ACID HYDROCARBYLSULFONYLHYDRAZONES AND THERAPEUTIC COMPOSITIONS

[75] Inventors: Edward W. Grange, Palo Alto, Calif.; David W. Henry, Chapel Hill, N.C.; William W. Lee, Palo Alto, Calif.

[73] Assignee: SRI International, Menlo Park, Calif.

[21] Appl. No.: 887,474

[22] Filed: Apr. 17, 1978

[51] Int. Cl.$^2$ .................... A61K 31/38; A61K 31/16; A61K 31/15; C07O 333/24

[52] U.S. Cl. .................................. 424/275; 424/320; 424/327; 260/569; 260/583 R; 549/65

[58] Field of Search ................ 260/332.2 A; 424/275, 424/320, 327

[56] References Cited

PUBLICATIONS

House "Chemical Abstracts", vol. 68, (1968), p. 39184s.
Blankley "Chemical Abstracts", vol. 72, (1970), p. 120977g.

*Primary Examiner*—Alan Siegel
*Attorney, Agent, or Firm*—Donovan J. De Witt

[57] ABSTRACT

Glyoxylic acid hydrocarbylsulfonylhydrazones and therapeutic compositions containing the same. Said compounds are useful in treating cancer, they being active against leukemia P-388, for example.

2 Claims, No Drawings

GLYOXYLIC ACID HYDROCARBYLSULFONYLHYDRAZONES AND THERAPEUTIC COMPOSITIONS

BACKGROUND OF INVENTION

The invention described herein was made in the course of or under a contract with the U.S. Department of Health, Education, and Welfare.

The nearest known prior art is the article of Herbert O. House and C. John Blankley, "Preparation and Decomposition of Unsaturated Esters of Diazoacetic Acid" published in The Journal of Organic Chemistry, Vol. 33, No. 1, January, 1968, pages 53–60. This article discloses the compound p-toluenesulfonylhydrazone. No therapeutic utility is ascribed to this compound or to the others which are disclosed.

SUMMARY OF INVENTION

The present invention rests in part on the discovery that glyoxylic acid hydrocarbylsulfonylhydrazone compounds have utility as anticancer agents when administered to cancerous warm-blooded animals. In one embodiment, this aspect of the invention relates to a process for treating leukemia which comprises administering to a warm-blooded animal having an abnormal proportion of leukocytes a therapeutic amount of a glyoxylic acid hydrocarbylsulfonylhydrazone compound. The latter compounds can be administered per se, or in association with a pharmaceutically acceptable diluent or carrier. The invention accordingly also provides a pharmaceutical composition in dosage unit form comprising from about 0.1 to 500 mg of the active compound, per dosage unit, together with a pharmaceutically acceptable nontoxic, inert carrier or diluent therefor. Lastly, the present invention discloses particular novel compounds coming within the scope of the broad class of glyoxylic acid hydrocarbylsulfonylhydrazone compounds which have utility as anticancer agents.

The novel compounds of the invention are those wherein the hydrocarbyl group is an aryl, alkyl or alkenyl group, whether substituted or unsubstituted, as set forth below in Table 1. In said table, the old compound of the prior art is given the number (1), with the novel compounds being numbered from (2) through (17).

TABLE 1

Hydrocarbyl-$SO_2NHN=CH-CO_2H$

| Compound No. | Hydrocarbyl Group |
|---|---|
| 1 | p-tolyl |
| 2 | phenyl |
| 3 | p-chlorophenyl |
| 4 | p-methoxyphenyl |
| 5 | m-nitrophenyl |
| 6 | 2,5-dichlorophenyl |
| 7 | β-naphthyl |
| 8 | m-aminophenyl |
| 9 | p-acetamidophenyl |
| 10 | 2,4,6-trimethylphenyl |
| 11 | phenyl,1,3-bis |
| 12 | 2-thienyl |
| 13 | styryl |
| 14 | benzyl |
| 15 | methyl |
| 16 | n-butyl |
| 17 | n-hexadecyl |

In general, the novel compounds of the present invention can readily be prepared by reacting the known hydrocarbylsulphonylhydrazide with glyoxylic acid, usually present in excess. The acid is normally employed in monohydrate form. Typical reaction temperatures range from about 5° C. to room temperature. The reaction is conducted for one or more hours, usually in the presence of an organic solvent, though in some cases aqueous solutions are employed. The product can be recovered by evaporation of the solvent. When aqueous media are employed, the product precipitates out as formed, it being water insoluble except when present in salt form (compound 8). The products are all white crystalline solids which melt with decomposition. They are soluble in many organic solvents such as acetonitrile, DMF, DMSO, dioxane, ethanol and methanol.

The examples which follow detail the preparation of each of the compounds shown in Table 1. The example numbers correspond to those by which each such compound is identified in said table.

EXAMPLE 1

GLYOXYLIC ACID p-TOLUENESULFONYLHYDRAZONE

A mixure of p-toluenesulfonylhydrazide (1.86 g, 10 mmol), glyoxylic acid monohydrate (1.20 g, 13 mmol), concentrated hydrochloric acid (1 cc, 12 mmol), and acetonitrile (40 cc) was stirred overnight at room temperature. The solvent was removed in vacuo and the residue triturated with water. The resulting white crystalline solid was collected by filtration and air dried to give 2.2 g of compound 1, m.p. 150° (dec.). Here, as in the other examples, the product compound is identified by elemental analysis as well as by IR and NMR methods.

EXAMPLE 2

GLYOXYLIC ACID BENZENESULFONYLHYDRAZONE

To a stirred, room temperature solution of 1.48 g (0.02 M) glyoxylic acid monohydrate in 20 cc of water was added, in one portion, a room temperature solution of 3.44 g (0.02 M) of benzenesulfonylhydrazide in 10 cc of 2.5 N HCl. The mixture turned milky and was followed by a white precipitate within a minute. After stirring for 2 hrs, the mixture was filtered and the precipitate was collected, washed with water and (sparingly) with methanol in which the compound is very soluble. After drying the desired product was obtained (3.54 g) as a white crystalline powder, m.p. 130°–3° (dec.).

EXAMPLE 3

GLYOXYLIC ACID p-CLOROBENZENESULFONYLHYDRAZONE

The subject compound is prepared using the general method of Example 1 except that 6.2 g (30 mmol) of p-chlorobenzenesulfonylhydrazide was reacted with 3.6 g (39 mmol) of glyoxylic acid monohydrate in the presence of 3 cc conc. HCl and 120 cc acetylnitrile. The product obtained (7.3 g) was a white crystalline material having a melting point of 163° (dec.).

EXAMPLE 4

GLYOXYLIC ACID p-METHOXYBENZENESULFONYLHYDRAZONE

The subject compound is prepared using the general method of Example 1 except that 6.06 g (30 mmol) of p-methoxybenzenesulfonylhydrazide was reacted with 3.6 g (39 mmol) of glyoxylic acid monohydrate in the presence of 3 cc conc. HCl and 120 cc acetonitrile. There was recovered 5.5 g of a white crystalline product having a melting point of 163° (dec.).

EXAMPLE 5
GLYOXYLIC ACID m-NITROBENZENESULFONYLHYDRAZONE

The subject compound was prepared using the general method of Example 1 except that 2.17 g (10 mmol) of n-nitrobenzenesulfonylhydrazide was reacted with 1.2 g (13 mmol) glyoxylic acid monohydrate in the presence of 1.0 c conc. HCl and 40 cc acetonitrile. There was recovered 2.4 g of the desired product, m.p. 164° (dec.).

EXAMPLE 6
GLYOXYLIC ACID 2,5-DICHLOROBENZENESULFONYLHYDRAZONE

The subject compound was prepared using the general method of Example 1 except that a mixture of 2,5-dichlorobenzenesulfonylhydrazide (2.41 g, 10 mmol) and glyoxylic acid monohydrate (1.20 g, 13 mmol) was stirred overnight at room temperature in the presence of conc. HCl (1 cc, 12 mmol) and acetonitrile (40 cc). The solvent was removed in vacuo and the residue was triturated with water. The resulting white, crystalline solid was collected by filtration and air dried to give 2.8 g of the desired product, m.p. 144° (dec.).

EXAMPLE 7
GLYOXYLIC ACID β-NAPHTHYLSULFONYLHYDRAZONE

The subject compound is prepared using the general method of Example 1 except that 4.4 g (20 mmol) of β-naphthylsulfonylhydrazide was reacted with 2.4 g (26 mmol) of glyoxylic acid monohydrate in the presence of 1 cc conc. HCl and 100 cc acetonitrile. The desired white crystalline product was obtained in a yield of 5.1 g, m.p. 149° (dec.).

EXAMPLE 8
GLYOXYLIC ACID 3-AMINOBENZENESULFONYLHYDRAZONE HYDROCHLORIDE

Glyoxylic acid monohydrate (966 mg, 10.5 mmol) was added all at once to a stirred mixture of 3-aminobenzenesulfonylhydrazide (1.8 g, 10 mmol), conc. HCl (1.9 cc, 22 mmol), and dioxane (50 cc). The reaction mixture was stirred for 1 hr, cooled, and the precipitated white crystalline solid collected by filtration. The product was washed with dioxane, then with ether and air dried to give 2.4 g of the desired product, m.p. 123° (dec.).

EXAMPLE 9
GLYOXYLIC ACID p-ACETAMIDOBENZENESULFONYLHYDRAZONE

The subject compound is prepared using the general method of Example 1 except that 4.58 g (20 mmol) of glyoxylic acid p-acetamidobenzenesulfonylhydrazide was reacted with 2.4 g (26 mmol) of glyoxylic acid monohydrate in the presence of ½ cc conc. HCl and 200 cc acetonitrile. The desired product was obtained in a yield of 5.4 g, m.p. 136° (dec.).

EXAMPLE 10
GLYOXYLIC ACID 2,4,6-TRIMETHYLBENZENESULFONYLHYDRAZONE

The subject compound is prepared using the general method of Example 1 except that 6.43 g (30 mmol) of 2,4,6-trimethylbenzenesulfonylhydrazide is reacted with 3.5 g (39 mmol) diglyoxylic acid monohydrate in the presence of 15 drops conc. HCl and 150 cc acetonitrile. The desired white crystalline product was obtained in a yield of 7.7 g, m.p. 153° (dec.).

EXAMPLE 11
DIGLYOXYLIC ACID 1,3-BENZENESULFONYLHYDRAZONE

The subject compound is prepared using the general method of Example 1 except that no conc. HCl was used. In the reaction, 4.8 g (52 mmol) of glyoxylic acid monohydrate were reacted with 5.3 g (20 mmol) of benzenesulfonylhydrazide in the presence of 200 cc acetonitrile. The method gave the product compound in the amount of 6.2 g as a white crystalline solid m.p. 178° (dec.).

EXAMPLE 12
GLYOXYLIC ACID 2-THIENYLSULFONYLHYDRAZONE

The subject compound is prepared using the general method of Example 1 except that no conc. HCl is employed. In this operation, 7.13 g (40 mmol) of 2-thienylsulfonylhydrazide is reacted with 4.42 g (48 mmol) of glyoxylic acid monohydrate in the presence of 160 cc acetonitrile. The desired product is recovered as a white crystalline material, m.p. 103° (dec.).

EXAMPLE 13
GLYOXYLIC ACID β-STYRENESULFONYLHYDRAZONE

In this operation a suspension of 1-formyl-2-(β-styrenesulfonyl)hydrazine (4.98 g, 22 mmol) in 6 N HCl (44 cc) was stirred for 4.5 hr at 50°–55° C. After cooling a small amount of insoluble material was removed by filtration. The filtrate was added all at once to a stirred solution of glyoxylic acid monohydrate (2.4 g, 26 mmol) in water (180 cc), and stirring was continued for 3 hr. The white crystalline solid which had precipitated was collected by filtration and air dried to give 3.0 g of the product compound, m.p. 141° (dec.).

EXAMPLE 14
GLYOXYLIC ACID BENZYLSULFONYLHYDRAZONE

The subject compound is prepared using the general method of Example 1 except that 3.72 g (20 mmol) of benzylsulfonylhydrazide is reacted with 2.39 g (26 mmol) glyoxylic acid monohydrate in the presence of 0.5 cc conc. HCl and 75 cc of acetonitrile. There is recovered 4.6 g of the desired white crystalline product compound, m.p. 140° (dec.).

EXAMPLE 15

GLYOXYLIC ACID METHANESULFONYLHYDRAZONE

In this operation methanesulfonylhydrazide (2.20 g, 20 mmol) was added all at once to a vigorously stirred suspension of glyoxylic acid monohydrate (2.02 g, 22 mmol) in dioxane (2 cc) and ether (8 cc). After stirring for 0.5 hr the reaction mixture was diluted with additional ether (10 cc). The upper solvent layer was removed by decantation and the residue was triturated with cold ether. The resulting white crystalline solid was collected by filtration and air dried to give 1.8 g of the desired white crystalline product, m.p. 154° C. (dec.).

EXAMPLE 16

GLYOXYLIC ACID 1-BUTANESULFONYLHYDRAZONE

A mixture of 1-butanesulfonylhydrazide (6.0 g, 40 mmol), glyoxylic acid monohydrate (4.4 g. 48 mmol), and ethyl acetate (90 cc) was stirred for 1 hr and then diluted with additional ethyl acetate (90 cc). The organic solution was twice washed with water using 20 cc portions. The organic solution was dried (MgSO$_4$) and the solvent was removed in vacuo to give a solid. After trituration with benzene, the white crystalline solid was collected by filtration and air dried to give 5.1 g, m.p. 142° C. (dec.).

EXAMPLE 17

GLYOXYLIC ACID n-HEXADECANESULFONYLHYDRAZONE

The subject compound was prepared using the general method of Example 1 except that no conc. HCl is employed. The preparation is carried out by reacting 3.2 g (10 mmol) of n-hexanedecanesulfonylhydrazide with 1.3 g (14 mmol) glyoxylic acid monohydrate in the presence of 200 cc acetonitrile. There is recovered 3.4 g of the desired product compound in the form of a white crystalline material, m.p. 144° (dec.).

The compound of example 8 was prepared in the form of a water-soluble, acid addition salt. While HCl was employed in this example as the salt forming acid, other pharmaceutically acceptable, non-toxic addition salts with acids such as nitric, sulfuric, phosphoric, glycolic could be used.

The compounds used in a practice of this invention, including any salts thereof, can be administered to the animal by any available route, including oral and parenteral (intravenous, intraperitoneal, subcutaneous, and intramuscular) administration. The amount administered is sufficient to ameliorate the leukemia or other type of cancer against which the compounds hereof may prove to be effective, and will depend upon the type of cancer, the species of animal, and the weight of the animal. A dosage of a compound of the present invention within the range from about 0.1 mg to about 500 mg per day per kg of body weight is therapeutic to ameliorate leukemia in the treatment of warm-blooded animals having an abnormal proportion of leukocytes. The upper dosage limit is that imposed by toxic side effects.

To facilitate administration, the compounds employed in a practice of this invention, including the salts thereof, can be provided in composition form, and preferably in dosage unit form. While any compound selected can be administered per se, it is normally administered in conjunction with a pharmaceutically acceptable carrier therefor, which dilutes the compound and facilitates handling. The term "pharmaceutically acceptable" means that the carrier (as well as the resulting composition) is sterile and nontoxic.

The carrier or diluent can be solid, semisolid, or liquid, and can serve as a vehicle, excipient, or medium for the anti-cancer agent. Exemplary diluents and carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan, monolaurate, methyl- and propyl-hydroxybenzoate, talc or magnesium stearate.

For convenience in handling, the compounds employed in a practice of this invention and the carrier or diluent can be enclosed or encapsulated in a capsule, sachet, cachet, gelatin, paper or other container, especially when intended for use in dosage units. The dosage units can for example take the form of tablets, capsules, suppositories or cachets.

The following examples illustrate various forms of dosage units in which the compound of Example 2 can be prepared, said compound being typical of the other compounds which can be employed in a practice of this invention.

EXAMPLE 18

| Tablet formulation | Mg/tablet |
|---|---|
| Compound (2) | 15 |
| Lactose | 86 |
| Cornstarch (dried) | 45.5 |
| Gelatin | 2.5 |
| Magnesium stearate | 1.0 |

Compound 2 is powdered and passed through a mesh sieve and well mixed with the lactose and 30 mg of the cornstarch, both passed through a sieve.

The mixed powders are massed with a warm gelatin solution, prepared by stirring the gelatin in water and heating to form a 10% w/w solution. The mass is granulated by passing through a sieve and the moist granules dried at 40° C.

The dried granules are regranulated by passing through a sieve and the balance of the starch and the magnesium stearate is added and thoroughly mixed.

The granules are compressed to produce tablets each weighing 150 mg.

EXAMPLE 19

| Tablet formulation | Mg/tablet |
|---|---|
| Compound (2) | 100 |
| Lactose | 39 |
| Cornstarch (dried) | 80 |
| Gelatin | 4.0 |
| Magnesium stearate | 2.0 |

The method of preparation is identical with that of Example 2 except that 60 mg of starch is used in the granulation process and 20 mg during tableting.

EXAMPLE 20

| Capsule formulation | Mg/tablet |
|---|---|
| Compound 2 | 250 |
| Lactose | 150 |

Compound 2 and lactose are passed through a sieve and the powders well mixed together before filling into hard gelatin capsules of suitable size, so that each capsule contains 400 mg of mixed powders.

EXAMPLE 21

| Suppositories | Mg/suppository |
|---|---|
| Compound 2 | 50 |
| Oil of Theobroma | 950 |

Compound 2 is powdered and passed through a sieve and triturated with molten oil of theobroma at 45° C. to form a smooth suspension. The mixture is well stirred and poured into molds, each of nominal 1 g capacity, to produce suppositories.

EXAMPLE 22

| Cachets | Mg/cachet |
|---|---|
| Compound 2 | 100 |
| Lactose | 400 |

Compound 2 is passed through a mesh sieve, mixed with lactose previously sieved and fitted into cachets of suitable size so that each contains 500 mg.

EXAMPLE 23

| Intramuscular injection (sterile suspension in aqueous vehicle) | Mg |
|---|---|
| Compound (2) | 10 |
| Sodium citrate | 5.7 |
| Sodium carboxymethyl-cellulose (low viscosity grade) | 2.0 |
| Methyl para-hydroxybenzoate | 1.5 |
| Propyl para-hydroxybenzoate | 0.2 |
| Water for injection to 1.0 ml | |

EXAMPLE 24

| Intraperitoneal, intravenous or subcutaneous injection (sterile solution in aqueous carrier system) | Mg |
|---|---|
| Compound (8) hydrochloric acid addition salt | 15 |
| Sodium citrate | 5.7 |
| Sodium carboxymethyl-cellulose (low viscosity grade) | 2.0 |
| Methyl para-hydroxybenzoate | 1.5 |
| Propyl para-hydroxybenzoate | 0.2 |
| Water for injection to 1.0 ml | |

The other compounds useful in a practice of this invention can be prepared in dosage unit form in the same general fashion as that described above for compound 2.

BIOLOGICAL TESTS

Biological testing data for the compounds of this invention are presented in the table given below. Said data were obtained when these compounds were tested against lymphocytic leukemia P388 implanted in mice under the auspices of the National Cancer Institute (NCI) and according to protocols which use the increased survival time of treated animals compared to controls as the measure of antitumor efficiency. In carrying out these tests, the various doses were administered ip in the form of aqueous dispersions or emulsions, the latter being formed in many cases with the aid of hydroxypropylcellulose.

Table 2

BIOASSAY DATA OF SUBJECT COMPOUNDS
Hydrocarbyl-$SO_2NHN=CH-CO_2H$

| Cpd. No. | NSC No.[a] | Hydrocarbyl Group | Activity vs. Leukemia P388 in Mice[b] qd 1-9, % T/C for Doses (mg/kg) | | | | | | |
|---|---|---|---|---|---|---|---|---|---|
| | | | 400 | 200 | 100 | 50 | 25 | 12.5 | 6.25 |
| 1 | 176331 | p-tolyl | | | | 165[c] | | | |
| 2 | 245422 | phenyl | | tox | 99 | 138 | 131 | 113 | |
| | | | | | 163[d] | 153 | 137 | 128 | |
| 3 | 267212 | p-chlorophenyl | 1/6[e] | 2/6 | 0/6 | 134 | 134 | 122 | |
| | | | | | 99 | 159 | 142 | 126 | 101 |
| 4 | 267213 | p-methoxyphenyl | 0/6 | 2/6 | tox | 158 | 149 | 141 | |
| | | | | | tox | 159 | 162 | 128 | 116 |
| 5 | 268244 | m-nitrophenyl | 3/6 | 160 | 141 | 134 | 122 | 138 | |
| | | | 3/6 | tox | 137 | 117 | 119 | | |
| | | | 4/6 | tox | 130 | 131 | 118 | | |
| 6 | 268245 | 2,5-dichlorophenyl | tox | tox | 130 | 132 | 119 | 114 | |
| | | | tox | 137 | 155 | 122 | 122 | 102 | |
| | | | tox | tox | tox | 121 | 119 | 109 | |
| 7 | 274883 | β-Naphthyl | 4/6 | 153 | 196 | 164 | 146 | 135 | |
| | | | 0/6 | tox | 90 | 161 | 144 | 136 | |
| 8 | 274884 | m-aminophenyl | 1/6 | tox | 117 | 119 | 116 | 111 | |
| 9 | 276745 | p-acetamidophenyl | 4/6 | 4/6 | tox | tox | 135 | 135 | |
| | | | | 3/6 | tox | 146 | 137 | 118 | 111 |
| 10 | 278173 | 2,4,6-trimethylphenyl | 1/6 | 3/6 | tox | 137 | 122 | 112 | |
| | | | | tox | 154 | 137 | 126 | 117 | |
| 11 | 279507 | phenyl, 1,3-bis | 0/6 | 3/6 | tox | 128 | 130 | 119 | |
| | | | | tox | tox | 143 | 133 | 127 | |

Table 2-continued

BIOASSAY DATA OF SUBJECT COMPOUNDS
Hydrocarbyl-SO$_2$NHN=CH—CO$_2$H

| Cpd. No. | NSC No.[a] | Hydrocarbyl Group | Activity vs. Leukemia P388 in Mice[b] qd 1-9, % T/C for Doses (mg/kg) | | | | | | |
|---|---|---|---|---|---|---|---|---|---|
| | | | 400 | 200 | 100 | 50 | 25 | 12.5 | 6.25 |
| 12 | 279506 | 2-thienyl | 1/6 | 2/6 | 149 | 137 | 127 | 119 | |
| | | | 0/6 | 4/6 | 136 | 130 | 130 | | |
| 13 | 285698 | styryl | 0/6 | tox | 186 | 155 | 140 | 129 | |
| 14 | 273425 | benzyl | tox | 166 | 185 | 142 | 129 | 127 | |
| | | | tox | 154 | 147 | 146 | 128 | 139 | |
| 15 | 276744 | methyl | 0/6 | 0/6 | tox | 125 | 119 | 114 | |
| | | | | tox | 159 | 126 | 127 | 118 | |
| | | | 0/6 | 3/6 | 157 | 160 | 134 | | |
| 16 | 276743 | n-butyl | 0/6 | 3/6 | tox | 132 | 126 | 114 | |
| | | | | tox | 172 | 162 | 135 | 124 | 119 |
| | | | 0/6 | tox | tox | 136 | 136 | | |
| 17 | 283459 | n-hexadecyl | 0/6 | 2/6 | 4/6 | 145 | 125 | 116 | |
| | | | 0/6 | tox | 140 | 131 | 129 | | |

[a]NSC accession number of the National Cancer Institute.
[b]Ip P388 murine leukemia treated ip on QD1-9 schedule according to standard NCI protocols. Assay described in R. I. Geran, N. H. Greenberg, M. M. MacDonald, A. M. Schumacher and B. J. Abbott, Cancer Chemother. Rep., Part 3, 3 (No. 2), 9 (1972), Protocol 1,200. T/C = ratio of survivial time of treated mice to that of untreated controls times 100. Untreated controls survive about 9 days.
[c]Average of 28 assays.
[d]Dosages were 75, 50, 32 and 20 mg/kg for this test.
[e]The indicia such as 0/6, 1/6, 2/6, etc. show no. survivors/no. test animals as toxicity day survivors (4 days after day of first injection).

What is claimed is:

1. A process for treating leukemia which comprises administering to a warm-blooded animal having an abnormal proportion of leukocytes a therapeutic non-toxic amount of at least one compound selected from the group consisting of glyoxylic acid p-toluenesulfonylhydrazone, glyoxylic acid benzenesulfonylhydrazone, glyoxylic acid p-clorobenzenesulfonylhydrazone, glyoxylic acid p-methoxybenzenesulfonylhydrazone , glyoxylic acid-m-nitrobenzenesulfonylhydrazone, glyoxylic acid 2,5-dichlorobenzenesulfonylhydrazone, glyoxylic acid β-naphthylsulfonylhydrazone, glyoxylic acid 3-aminobenzenesulfonylhydrazone · HCl, glyoxylic acid p-acetamidobenzenesulfonylhydrazone, glyoxylic acid 2,4,6-trimethylbenzenesulfonylhydrazone, digyloxylic acid 1,3-benzenedisulfonylhydrazone, glyoxylic acid 2-thienylsulfonylhydrazone, glyoxylic acid β-styrenesulfonylhydrazone, glyoxylic acid benzylsulfonylhydrazone, glyoxylic acid methanesulfonylhydrazone, glyoxylic acid 1-butanesulfonylhydrazone or glyoxylic acid n-hexadecanesulfonylhydrazone.

2. A process according to claim 1 in which the compound is administered in an amount within a range of from about 0.1 to about 500 mg per day.

* * * * *